(12) United States Patent
McIlrath (10) Patent No.: US 12,179,006 B2
(45) Date of Patent: Dec. 31, 2024

(54) NEEDLE SENSOR ASSEMBLY AND METHOD OF USE OF SAME

(71) Applicant: TRACKER SYRINGE, LLC, Sherrill, IA (US)

(72) Inventor: Patrick McIlrath, Sherrill, IA (US)

(73) Assignee: TRACKER SYRINGE, LLC, Sherrill, IA (US)

( * ) Notice: Subject to any disclaimer, the term of this patent is extended or adjusted under 35 U.S.C. 154(b) by 708 days.

(21) Appl. No.: 17/426,318

(22) PCT Filed: Feb. 4, 2020

(86) PCT No.: PCT/US2020/016486
§ 371 (c)(1),
(2) Date: Jul. 28, 2021

(87) PCT Pub. No.: WO2020/163262
PCT Pub. Date: Aug. 13, 2020

(65) Prior Publication Data
US 2022/0160971 A1 May 26, 2022

Related U.S. Application Data (60) Provisional application No. 62/802,791, filed on Feb. 8, 2019.

(51) Int. Cl.
*A61M 5/50* (2006.01)
*A61M 5/32* (2006.01)

(52) U.S. Cl.
CPC .......... *A61M 5/5086* (2013.01); *A61M 5/322* (2013.01); *A61M 2202/30* (2013.01);
(Continued)

(58) Field of Classification Search
CPC ...... A61M 2205/18; A61M 2205/3306; A61M 2205/3317; A61M 2205/3375;
(Continued)

(56) References Cited

U.S. PATENT DOCUMENTS 4,624,658 A  11/1986  Mardorf et al.
6,171,276 B1 *  1/2001  Lippe ..................... A61M 5/20
                                                           604/67

(Continued)

FOREIGN PATENT DOCUMENTS

CN  101917901 A  12/2010
CN  104302336 A  1/2015
(Continued)

OTHER PUBLICATIONS

European Search Report dated Sep. 15, 2022 for related European Patent Application 20751963.8 (7 pgs).
(Continued)

*Primary Examiner* — Phillip A Gray
(74) *Attorney, Agent, or Firm* — STINSON LLP (57) ABSTRACT

The present invention is directed to a needle sensor assembly and a method of using same. The needle sensor assembly includes a needle sensor housed within the needle sensor assembly. The needle sensor assembly is configured to be attached to an injection device. When the needle sensor assembly is attached to the injection device, the needle sensor is configured to detect if a needle positioned for use in the injection device is misaligned, absent, or broken.

23 Claims, 10 Drawing Sheets

(52) U.S. Cl.
CPC . *A61M 2205/18* (2013.01); *A61M 2205/3306* (2013.01); *A61M 2205/3317* (2013.01); *A61M 2205/3375* (2013.01); *A61M 2205/8281* (2013.01); *A61M 2250/00* (2013.01)

(58) Field of Classification Search
CPC ...... A61M 2205/8281; A61M 2205/14; A61M 2205/13; A61M 5/20
See application file for complete search history.

(56) References Cited

U.S. PATENT DOCUMENTS

| | | | |
|---|---|---|---|
| 7,704,231 | B2 | 4/2010 | Pongpairochana et al. |
| 11,213,377 | B2* | 1/2022 | Monti, Jr. ............. A61M 5/326 |
| 2005/0197650 | A1 | 9/2005 | Sugimoto et al. |
| 2005/0261633 | A1* | 11/2005 | Khalaj .................... A61M 5/20 604/181 |
| 2011/0202012 | A1 | 8/2011 | Bartlett |
| 2014/0142537 | A1 | 5/2014 | Gibson et al. |
| 2016/0001016 | A1* | 1/2016 | Poulsen .............. A61M 5/3148 604/111 |
| 2016/0008556 | A1 | 1/2016 | Baym et al. |
| 2016/0058957 | A1 | 3/2016 | Brodsky et al. |
| 2016/0310164 | A1 | 10/2016 | Bertholds et al. |
| 2017/0106145 | A1 | 4/2017 | Sanofi |
| 2017/0274149 | A1* | 9/2017 | Aeschlimann ........... H04Q 9/00 |

FOREIGN PATENT DOCUMENTS

| | | |
|---|---|---|
| CN | 106413785 A | 2/2017 |
| CN | 106794316 A | 5/2017 |
| WO | 2017/145141 A1 | 8/2017 |

OTHER PUBLICATIONS

International Search Report and Written Opinion mailed on Apr. 29, 2020 for related application PCT/US2020/016486 (10 pgs).

* cited by examiner

NEEDLE SENSOR ASSEMBLY AND METHOD OF USE OF SAME

CROSS-REFERENCE TO RELATED APPLICATIONS

This application is based on and claims priority to U.S. Provisional Application Ser. No. 62/802,791 filed on Feb. 8, 2019, which is hereby incorporated herein by reference.

BACKGROUND OF THE INVENTION

1. Field of the Invention

The present invention is directed to a needle sensor assembly and its use in conjunction with an injection device.

2. Description of Related Art

In livestock production operations, animal health management protocols often require veterinarians and farm personnel to administer vaccines, supplements, and medicines to the animals. Among other methods, these products may be administered by adding solids or liquids to the animal's feed or water, nasal spray, or parenteral injection. Parenteral injection is common and includes intramuscular, subcutaneous, and intradermal injections into the animal's tissue. These injections are challenging because it is often difficult to restrain the animal, and large numbers of animals must be injected in a short period of time. In these settings, it is possible for the injection needle to break while the animal is being injected. This can happen when the injection needle is bent or weakened or when the animal moves and force is applied to the injection needle or injection device.

When a needle breaks during livestock injections, it is a serious food safety risk to the consumer. The broken needle may fall to the ground where animals may place the needle in their mouth or consume the needle. The broken needle may also remain in the animal at the injection site and stay in the animal until the animal is slaughtered. In these types of incidents, needle materials remain in the animal until slaughter and may not be discovered at the slaughterhouse. Broken needle incidents present serious risks to the meat consumer, as the meat may contain a needle that could injure the consumer if chewed or swallowed by the consumer. Broken needle incidents also present serious risks to the livestock and meat industries, because if a consumer comes in contact with a broken needle, it will portray the product and meat industry in a negative light. This may reduce demand for all meat products. A number of inventions have sought to reduce the risk of livestock broken needle incidents. These include needleless injection devices, stronger needles that are less prone to breakage, metal detection systems at meat processing plants, and needles that are more susceptible to detection by such metal detection systems at the processing plant. Needleless injection devices can completely eliminate the risk of livestock broken needle incidents, but the devices are complex and costly such that adoption of these products has been limited. Stronger needles may reduce the risk of breakage, but they do not eliminate it. Metal detection systems at the processing plant can detect some, but not all, broken needles in the meat. The detectability is limited and somewhat variable based on the size of the cut of meat, how the needle is positioned in meat and the types of metal that was used to manufacture the needle.

The livestock industry has determined that it is important to prevent broken needles at the source, which is the farm where the animals are raised. See, for example, the U.S. National Pork Board educational campaign for farm workers called "One is Too Many" which highlights the risk that a single broken needle could present to the industry as a whole.

However, mitigating the risk of broken needles on the farm is also challenging. A significant problem is that it is often not immediately apparent to the user that a needle is broken. It is uncommon and inefficient for workers to stop and inspect the needle after each injection, so there is a time lag between the breaking of the needle and its discovery. When a worker is in a pen or stable with more than one animal, they may inject animals one after the other, and not discover that their needle has broken until they have injected, or unsuccessfully attempted to inject, subsequent animals. This problem is exacerbated by the movement of animals within the pen or stable, which movement may increase when a worker is also present in the pen. Because a broken needle is typically not externally visible, by the time that the worker realizes that a portion of the needle is broken, the worker may not know which of the animals in the pen carries that broken needle in their tissue. This could lead to condemnation or euthanasia of a large number of animals, even though most of those animals do not carry a broken needle. It may also hamper corrective actions because of the large amount of labor associated with inspecting 50 or 100 animals in a pen to locate the broken needle.

Finally, it has been observed that livestock needles will occasionally become bent and that bent needles are more prone to breaking. Thus, preventing the use of bent needles would also reduce the risk of broken needles in the food supply.

BRIEF SUMMARY OF THE INVENTION

In a first aspect, the present invention is directed to a needle sensor assembly. The needle sensor assembly includes a needle sensor housed within the needle sensor assembly. The needle sensor assembly is configured to be attached to an injection device. When the needle sensor assembly is attached to an injection device, the needle sensor is configured to detect if a needle positioned for use in the injection device is misaligned, absent, or broken.

In certain embodiments, the needle sensor may be configured to be aligned with and facing the needle when the needle is positioned for use in the injection device.

In certain embodiments, the needle sensor may be a fiber optic sensor. The fiber optic sensor may be configured to generate an optical beam that extends in a plane that is aligned with the longitudinal axis of the needle when the needle is positioned for use in the injection device.

In certain embodiments, the needle sensor assembly may further include a movable arm on which the needle sensor is carried. The movable arm is movable between a first extended position and a second retracted position. When the movable arm is in the first extended position, the needle sensor is aligned with a portion of the needle when the needle is positioned for use in the injection device. The movable arm may extend generally parallel to a longitudinal axis of the needle when the needle is positioned for use in the injection device. The movable arm may be configured to slidably move generally parallel to a longitudinal axis of the needle when the needle is positioned for use in the injection device to maintain alignment of the needle sensor with the longitudinal axis of the needle.

In certain embodiments that include a movable arm, the needle sensor is a fiber optic sensor, and when the movable arm is in the first extended position, the optical beam aligns with at least a portion of the needle when the needle is positioned for use in the injection device.

In certain embodiments that include a movable arm, the needle sensor assembly may further comprise a spring. The spring is releasably biased against the movable arm when the movable arm is in the first extend position. The spring is forcibly biased by the movable arm when the movable arm is in the second retracted position. The needle sensor assembly may include a hollow cavity which houses the spring and that is configured to receive the movable arm. The needle sensor assembly may further include needle sensor wiring. At least a portion of the needle sensor wiring is positioned within the hollow cavity, and that portion of the needle sensor wiring may be coiled to prevent kinking. The needle sensor assembly may further include a sensor guide barrel within the hollow cavity. The spring is housed within the sensor guide barrel and the needle sensor wiring is coiled around the sensor guide barrel. The needle sensor assembly may further include a needle sensor wiring conduit between the hollow cavity and the exterior of the needle sensor assembly.

In certain embodiments, the needle sensor assembly includes a sensor system. The sensor system may include the needle sensor, the needle sensor wiring, a sensor amplifier unit, and a sensor electrical source. The sensor system may be configured to detect when a needle is positioned for use in the injection device. The sensor system may be configured to generate a warning when the needle is not detected.

In certain embodiments, the needle sensor assembly includes an adjustment mechanism configured to adjust a spacing between the needle sensor and the injection device when the movable arm is in the first extended position. The adjustment mechanism may include an adjustment core and an adjustment member. The adjustment core may be slidably positioned within a sensor guide barrel within a hollow cavity within the needle sensor assembly, and the lateral movement of the adjustment core within the sensor guide barrel may be limited. The adjustment member may have a proximal end adjustably attached to the adjustment core and a distal end connected to a distal end of the movable arm. The adjustment member may be a screw.

In a second aspect, the present invention is directed to a method of injecting a subject. The method includes the following steps: positioning an injection device against the skin of a subject, wherein a needle is positioned for use in the injection device and the needle sensor assembly is attached to an injection device; pressing a tip of the needle and a distal end of the movable arm against a skin of the subject, wherein the movable arm is in the first extended position; inserting the needle into the skin of the subject at the injection point, wherein as the needle is inserted, the movable arm is pushed to the second retracted position; withdrawing the needle from a subject, wherein the movable arm returns to the first extended position as the needle is withdrawn; wherein the needle sensor detects the presence or absence of a portion of the needle when the movable arm is returned to the first extended position; and wherein the needle sensor assembly generates a warning if the portion of the needle is not detected. Needle sensor wiring extending outside of the needle sensor assembly may be positioned in a space between a front body and a handle of the injection device.

Additional aspects of the invention, together with the advantages and novel features appurtenant thereto, will be set forth in part in the description that follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

In a first aspect, the present invention is directed to a needle sensor assembly. This aspect is described with relation to exemplary needle sensor assembly 10a shown in FIGS. 1-3, 5, and 6a-d, as attached to injection device 12, but is not limited to such embodiment. Needle sensor assembly 10 includes a needle sensor 14 housed within needle sensor assembly 10. Needle sensor assembly 10 is configured to be attached to an injection device 12. Together, needle sensor assembly 10 and injection device 12 are referred to herein as injector 16. A needle 18 is attached to and positioned for use with injection device 12. When needle sensor assembly 10 is attached to injection device 12, needle sensor 14 is configured to detect if needle 18 positioned for use in injection device 12 is misaligned, absent, or broken.

In certain embodiments, needle sensor 14 may be configured to be aligned with and facing needle 18 when needle 18 is positioned for use in injection device 12. This allows needle sensor 14 to detect whether the needle 18 is misaligned, absent, or broken.

In certain embodiments, needle sensor 14 may be a fiber optic sensor. The fiber optic sensor may be configured to generate an optical beam that extends in a plane that is aligned with the longitudinal axis of needle 18 when needle 18 is positioned for use in injection device 12. Needle sensor 14 may be any type of sensor that allows the detection of the presence or absence of needle 18. Needle sensor 14 may be a reflective fiber optic sensor, but other sensors may be utilized, including but not limited to a proximity sensor, an infrared sensor, a passive infrared sensor, an ultrasonic sensor, a magnetic sensor, an inductive sensor, or a capacitive sensor.

Referring to FIGS. 1-3, 5, and 6a-d, and as described more fully herein, needle sensor 14 is configured to detect when the needle 18 is positioned for use in injection device 12 and to generate a warning when the needle is not detected. In embodiments wherein needle sensor 14 is a fiber optic sensor, needle sensor 14 emits and receives light energy and converts this light energy into an electrical signal. As shown in FIGS. 6a-d, the light energy emitted may be an optical beam 20. Needle sensor 14 preferably has both a light emitting component and a light receiving component so that needle sensor 14 can determine the presence or absence of an object, such as needle 18, by the quantity of light that is received by the light receiving component.

Figure 5:
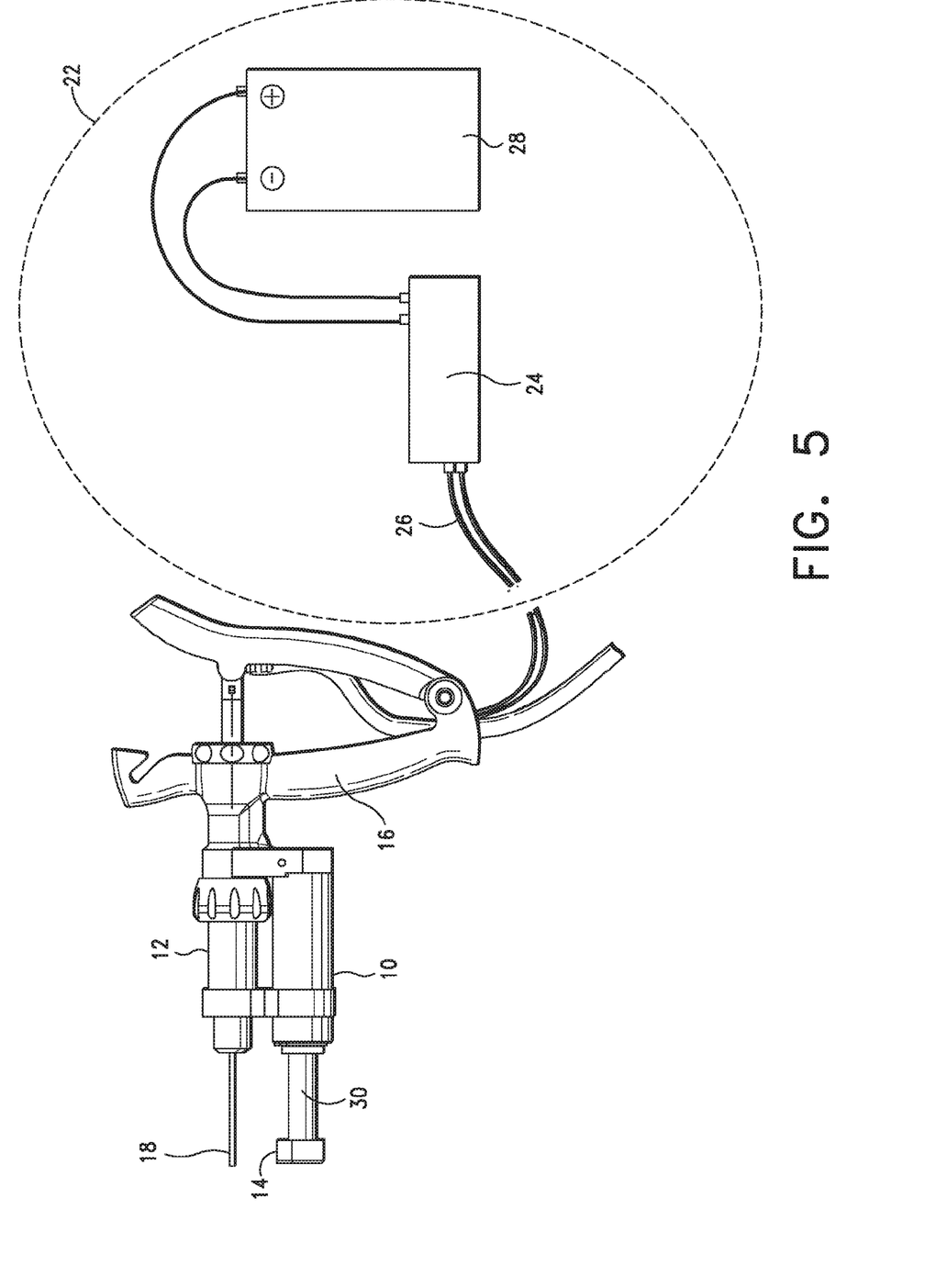
FIG. 5 is a side view of the injector of FIG. 1, wherein the needle sensor assembly further includes a sensor system.

In certain embodiments, needle sensor 14 is part of a sensor system 22, an exemplary embodiment of which is shown in FIG. 5. Referring to FIG. 5, sensor system 22 of needle sensor assembly 10 may include sensor amplifier unit 24, sensor wiring 26, and sensor electrical source 28. Sensor system 22 may be configured to detect when a needle is positioned for use in the injection device. The sensor system 22 may be configured to generate a warning when the needle is not detected, as will be understood by one of ordinary skill in the art.

In the exemplary embodiment shown in FIGS. 5 and 6a-d, sensor wiring 26 is connected to sensor amplifier unit 24 and needle sensor 14. Specifically, sensor amplifier unit 24 generates optical beam 20, and optical beam 20 travels through sensor wiring 26 and is emitted out of needle sensor 14. Sensor wiring 26 and needle sensor 14 allow optical beam 20 to reach remote or space-constrained areas. The interior portion of sensor wiring 26 may be plastic, glass or other material known in the art. Needle sensor 14 has both a light emitting component and a light receiving component so that sensor amplifier unit 24 and needle sensor 14 can determine the presence or absence of an object, such as needle 18, by the quantity of light that is received by the light receiving component. Sensor amplifier unit 24 converts this light energy into an electrical signal. When insufficient light is reflected back to sensor amplifier unit 24, sensor amplifier unit 24 generates an electrical output to an electromagnetic switch (not shown), or relay (not shown), which is connected to an alarm (not shown). When the electromagnetic switch receives the electrical output from sensor amplifier unit 24, the electromagnetic switch closes a second circuit (not shown) to provide electric current to sound or otherwise initiate the alarm.

Figure 6A:
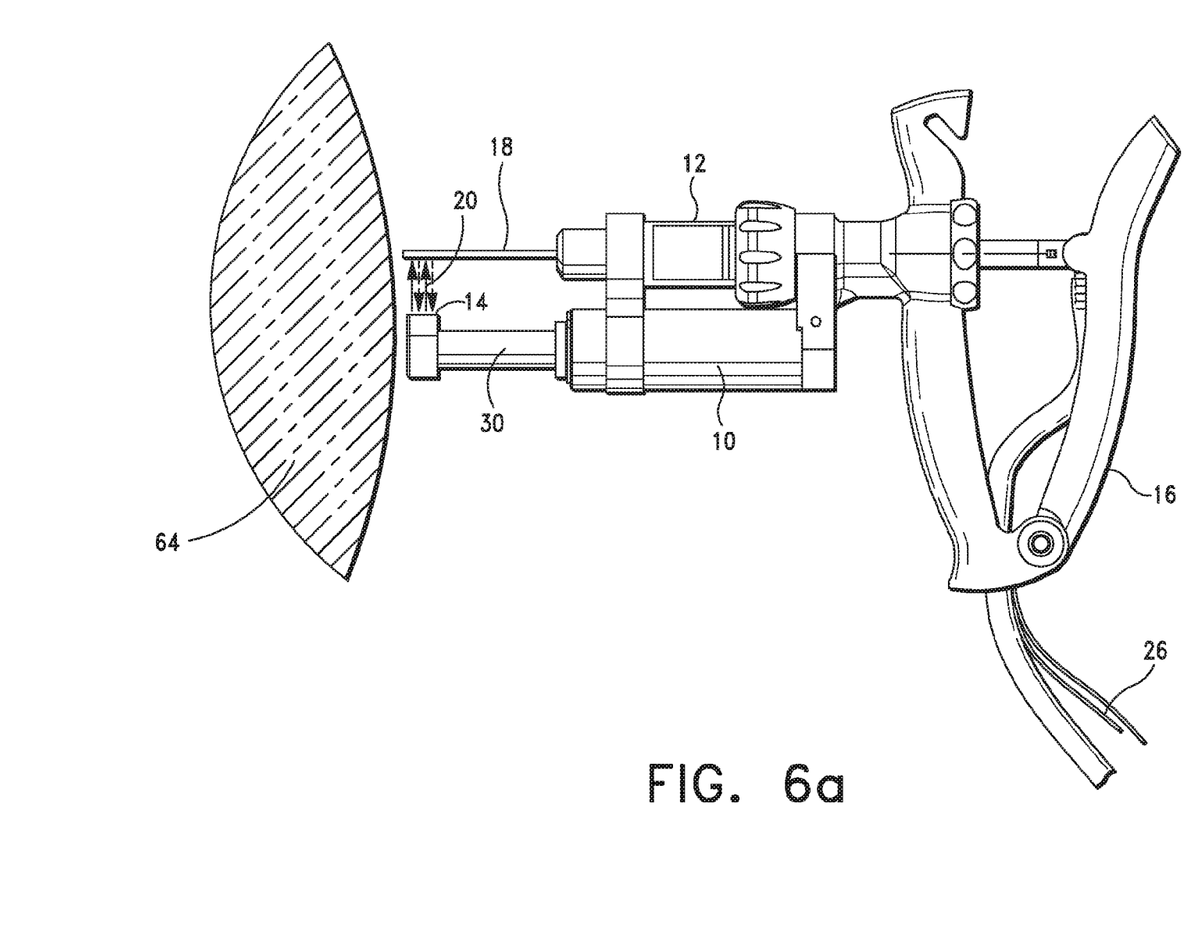
FIG. 6a is a side view of the injector of FIG. 1 prior to injecting a subject.
Figure 6B:
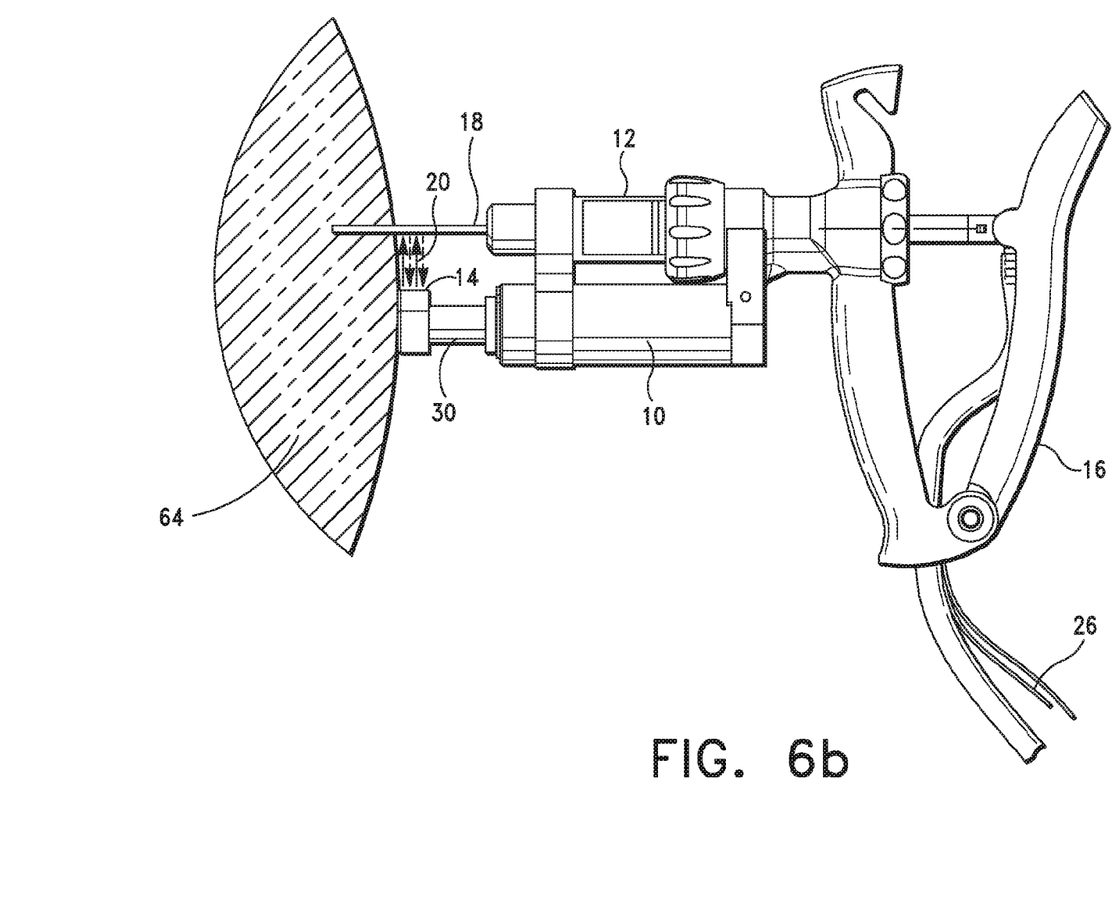
FIGS. 6b and 6c are side views of the injector of FIG. 1 during the injection of a subject.
Figure 6C:
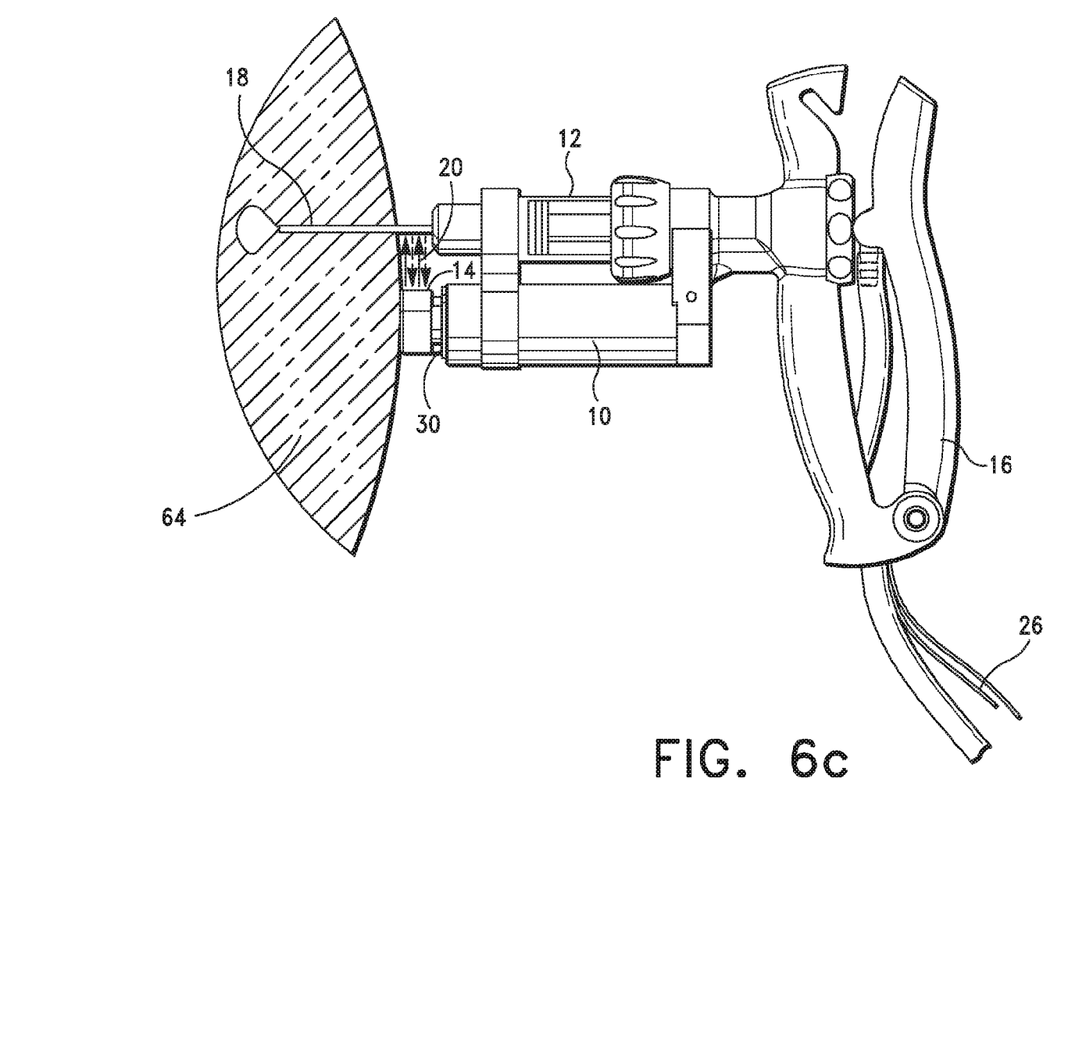
Figure 6D:
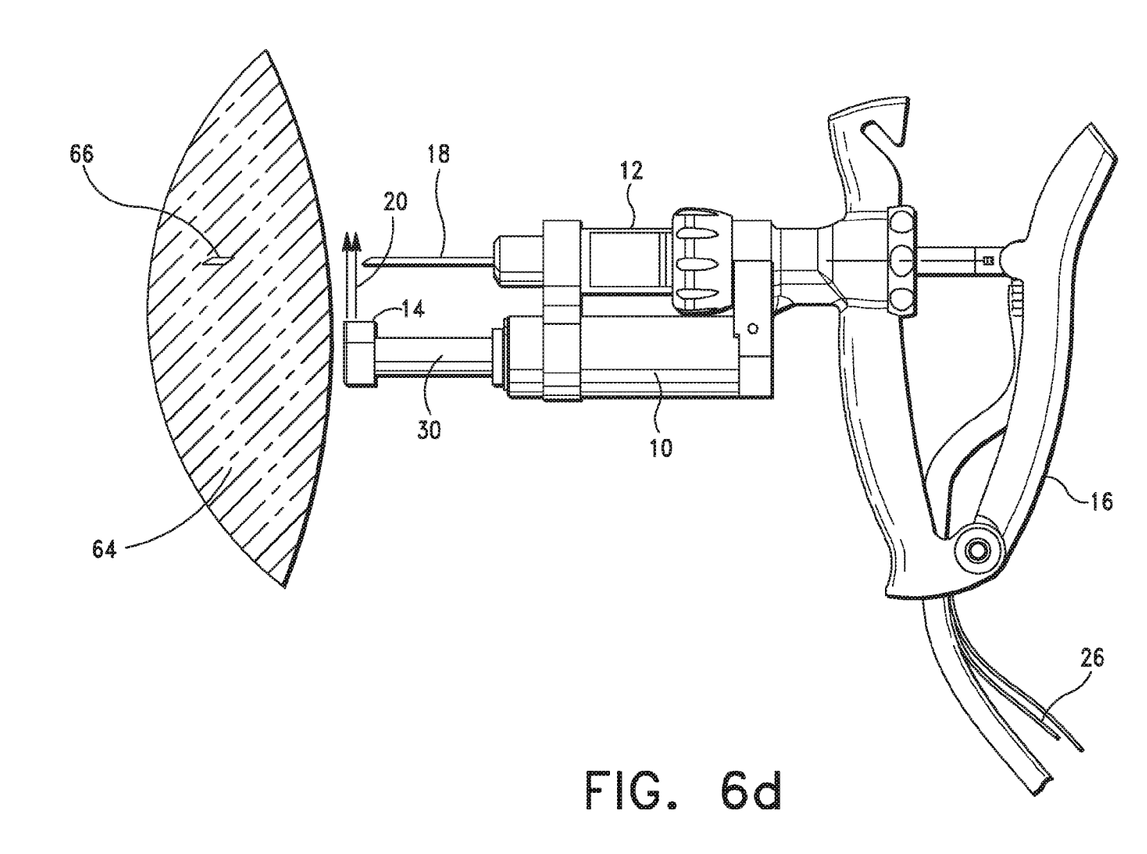
FIG. 6d is a side view of the injector of FIG. 1, wherein the needle attached to the injection device of the injector is broken.

In certain embodiments, and as shown in FIGS. 1-3, 5, and 6a-d, needle sensor assembly 10 may further include movable arm 30 on which needle sensor 14 is carried. Movable arm 30 is movable between a first extended position as shown in FIGS. 1-3, and 6a, and a second retracted position as shown in FIG. 6c. When movable arm 30 is in the first extended position, needle sensor 14 is aligned with a portion of a tip of needle 18 when needle 18 is positioned for use in the injection device 12. Movable arm 30 may extend generally parallel to a longitudinal axis of the needle 18 when needle 18 is positioned for use in injection device 12. Movable arm 30 may be configured to slidably move generally parallel to a longitudinal axis of needle 18 when needle 18 is positioned for use in injection device 12 to maintain alignment of needle sensor 14 with the longitudinal axis of needle 18. When movable arm 30 is in the first extended position, needle sensor 14 aligns with at least a portion of a tip of needle 18 when needle 18 is positioned for use in injection device 12 and detects when the tip of needle 18 is not present. When needle sensor 14 is an optical sensor, optical beam 20 aligns with at least a portion of a tip of needle 18 when movable arm 30 is in the first extended position.

Figure 1:
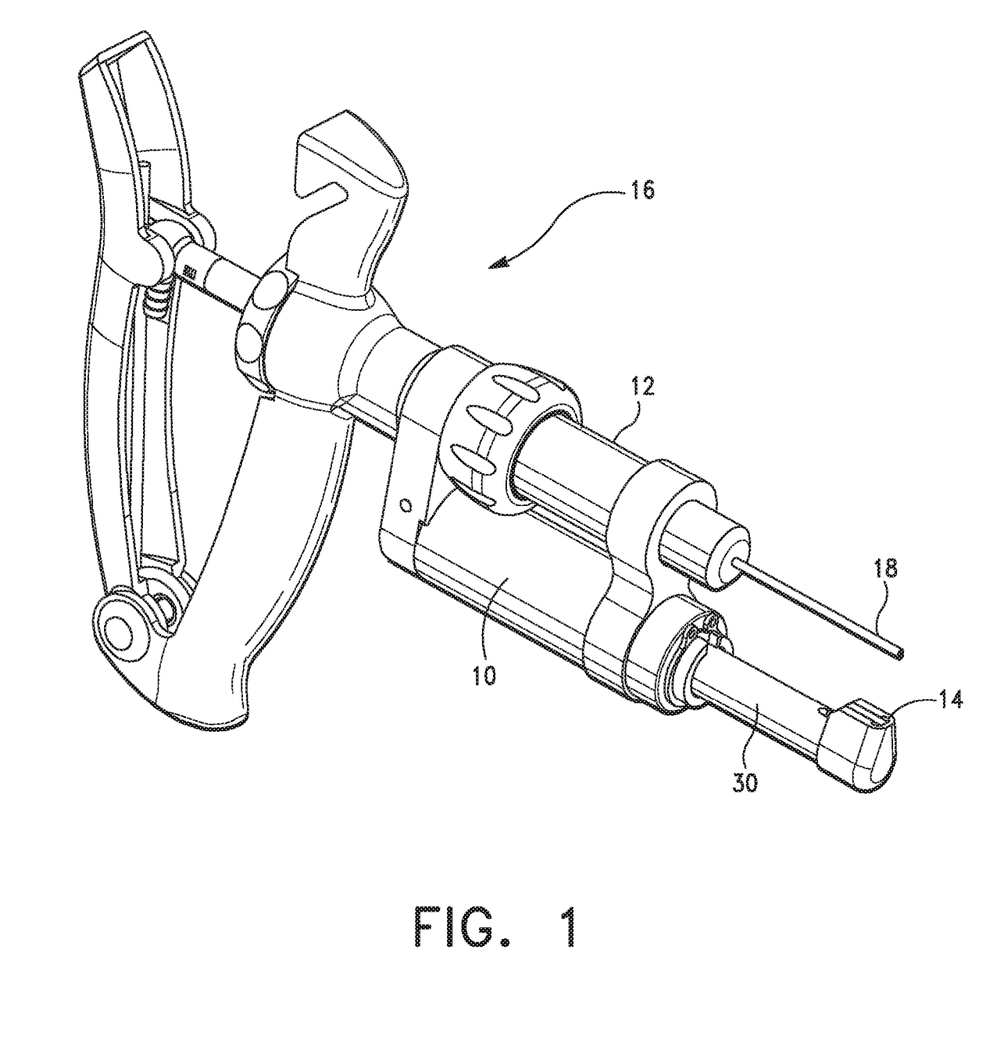
FIG. 1 is a perspective view of an exemplary embodiment of a needle sensor assembly attached to an injection device, which are referred to herein in combination as an "injector."
Figure 2:
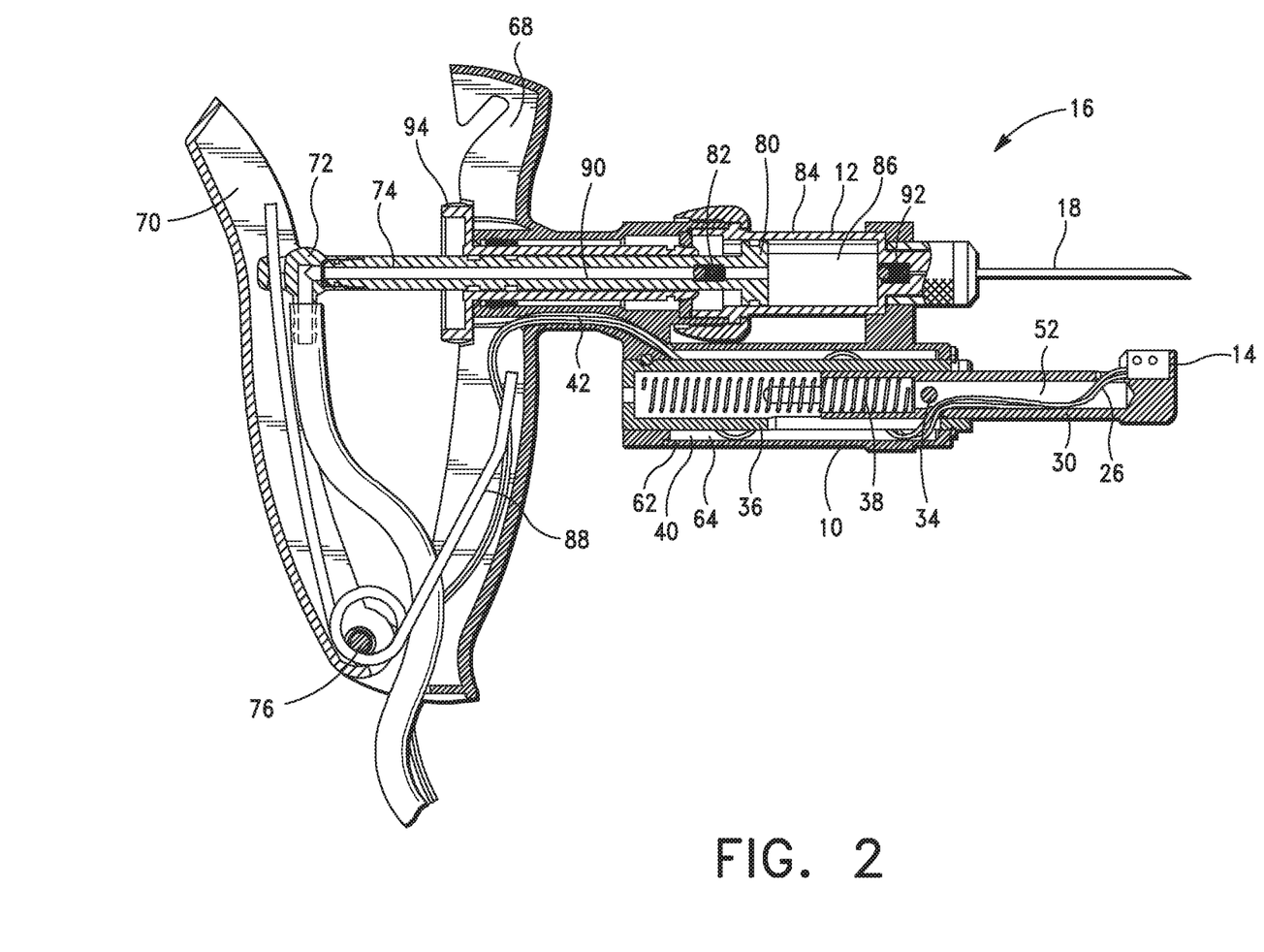
FIG. 2 is a cross-sectional view of the injector of FIG. 1.

With further reference to the exemplary embodiment shown in FIGS. 1-2, and 6a, when injector 16 is in the ready-to-inject position, movable arm 30 of needle sensor assembly 10 is in a first open/extended position. As described further herein, movable arm 30 is configured to slidably move generally parallel to a longitudinal axis of needle 18, which is positioned for use in injection device 12 of injector 16, in order to maintain alignment of needle sensor 14 with the longitudinal axis of needle 18. When movable arm 30 is in this open/extended position, movable arm 30 is releasably biased to its maximum forward position. Movable arm 30, in this maximum forward position, puts needle sensor 14 in alignment with and facing the tip of needle 18. The maximum forward position of movable arm 30 may be adjusted by adjustment mechanism 32, discussed in more detail below with respect to FIG. 7.

Figure 3:
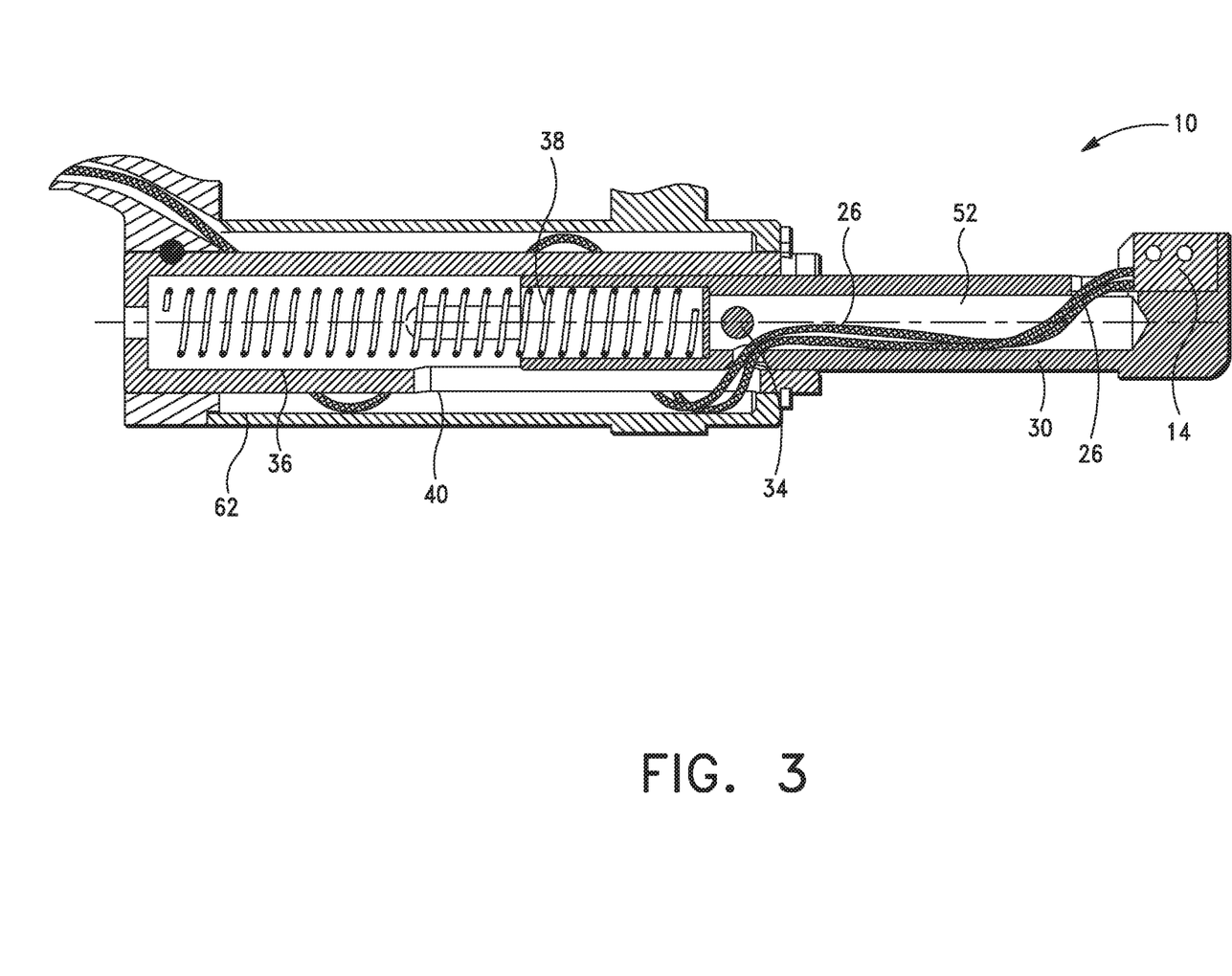
FIG. 3 is a partial cross-sectional view of the needle sensor assembly of the injector of FIG. 1.

Referring to FIGS. 2-3, needle sensor assembly 10 may include sensor needle alignment pin 34 that both limits the stroke of the movable arm 30 and keeps needle sensor 14 aligned with and facing needle 18. Because needle sensor 14 emits optical beam 20 in a single direction, it is important that needle sensor 14 emits optical beam 20 in the direction of needle 18. Sensor needle alignment pin 34 is secured in an opening in movable arm 30, such that sensor needle alignment pin 34 and movable arm 30 move in unison. Sensor needle alignment pin 34 extends through movable arm 30 and into sensor guide barrel 36, where sensor needle alignment pin 34 sits in opposite grooves of sensor guide barrel 36. This positioning of sensor needle alignment pin 34 in the grooves of sensor guide barrel 36 restricts the movement of sensor needle alignment pin 34 and moveable arm 26, such that these components move only distally and proximally. The same grooves of the sensor guide barrel 36 prevent rotational movement of sensor needle alignment pin 34 and movable arm 30, which ensures that optical beam 20 is emitted in the direction of the needle 18. Other mechanisms for maintaining needle sensor 14 aligned with and facing needle 18 may be used, as will be understood by those of ordinary skill in the art.

Referring to FIGS. 2, 5, and 6a, in the first open/extended position, movable arm 30, and sensor needle alignment pin 34 if present, position needle sensor 14 such that optical beam 20 emitted from needle sensor 14 is shone on at least a portion of the tip of needle 18. This allows needle sensor 14, via sensor amplifier unit 24 if present, to determine the presence or absence of at least a portion of needle 18. As explained herein, while movable arm 30 moves proximally and distally within its stroke, movable arm 30 and needle sensor 14 always maintain axial alignment with needle 18 and face needle 18. This ensures that optical beam 20 is always emitted towards some portion of needle 18, as long as needle 18 is present and properly positioned. Optical beam 20 generated by the needle sensor 14 extends in a plane that is aligned with the longitudinal axis of needle 18 when needle 18 is positioned for use in injection device 12. Optical beam 20 may be emitted towards a more proximal or distal portion of needle 18, because the target of optical beam 20 is determined by the position of movable arm 30 within the limits of the stroke of movable arm 30.

In certain embodiments that include a movable arm (such as movable arm 30), needle sensor assembly 10 may further include a spring, such as needle sensor return spring 38 shown in FIGS. 2-3. Spring 38 is releasably biased against movable arm 30 when movable arm 30 is in the first extend position. Spring 38 is forcibly biased by movable arm 30 when movable arm 30 is in the second retracted position. Needle sensor assembly 10 may include a hollow cavity 40 which houses spring 38 and that is configured to receive movable arm 30. Needle sensor assembly 10 may further include needle sensor wiring 26. At least a portion of needle sensor wiring 26 is positioned within hollow cavity 40, and that portion of needle sensor wiring 26 may be coiled to prevent kinking. Needle sensor assembly 10 may further include sensor guide barrel 36 within hollow cavity 40. Spring 38 is housed within sensor guide barrel 36 and needle sensor wiring 26 is coiled around sensor guide barrel 36. Needle sensor assembly 10 may further include needle sensor wiring conduit 42 between hollow cavity 40 and the exterior of the needle sensor assembly 10.

Figure 7:
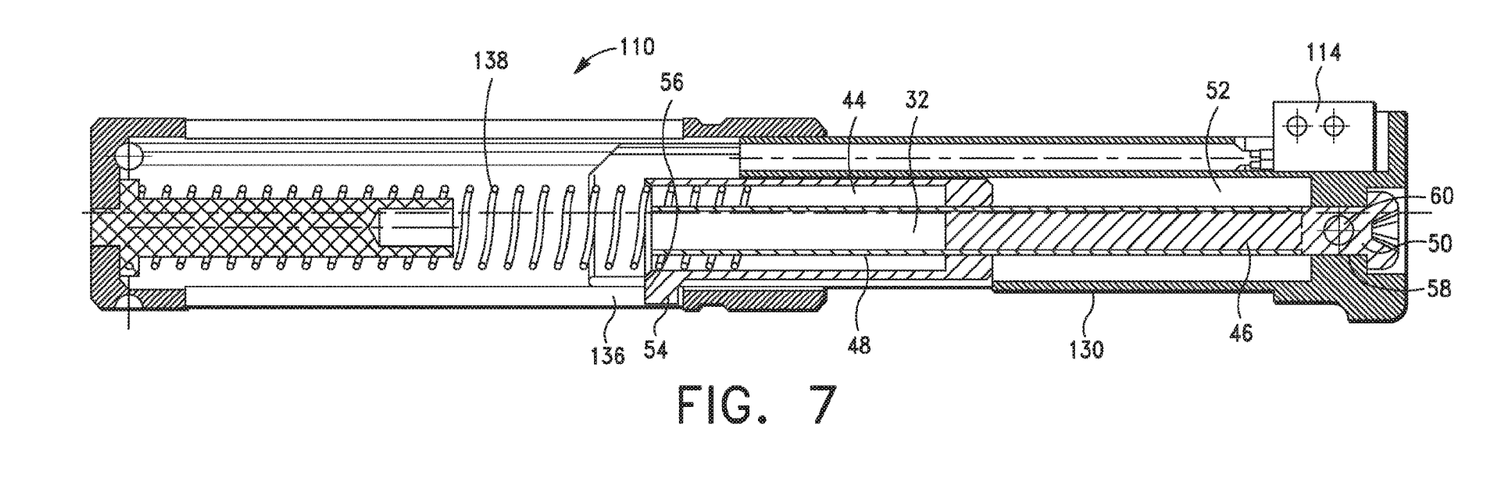
FIG. 7 is a first partial-cross sectional view of an alternative embodiment of the needle sensor assembly shown in FIG. 3.

In certain embodiments of the needle sensor assembly of the present invention that include a movable arm, the needle sensor assembly may further include an adjustment mechanism to adjust the maximum forward position of movable arm. As shown in FIG. 7, an alternative embodiment of the needle sensor assembly of the present invention is designated with numeral 110 and includes detachable adjustment mechanism 32. By adjusting the maximum forward position of movable arm 130, adjustment mechanism 32 adjusts the spacing between needle sensor 114 and the injection device (not shown in FIG. 7) when movable arm 130 is in the first extended position (shown in FIGS. 1-3, and 6a with needle sensor assembly 10 and movable arm 30) as needed in order to accommodate the length of a given needle (including but not limited to needle 18) positioned for use in injection device 12. Adjustment mechanism 32 does not affect the spacing between needle sensor 114 and injection device 12 when needle sensor assembly 110 is in the second retracted position (shown in FIG. 6c with needle sensor assembly 10 and movable arm 30).

Returning to FIG. 7, adjustment mechanism 32 includes an adjustment core 44 slidably positioned within sensor guide barrel 136, where lateral movement of adjustment core 44 within sensor guide barrel 136 is limited, and an adjustment member 46 having a proximal end adjustably attached to adjustment core 44 and a distal end connected to a distal end of movable arm 130. The proximal end of adjustable member 46 may be adjustably attached to adjustment core 44 in a manner that allows the proximal end of adjustable member 46 to extend an adjustable length into adjustment core 44. The spacing between needle sensor 114 and the injection device when movable arm 130 is in the first extended position is adjusted by adjusting the length adjustable member 46 extends into adjustment core 44.

As shown in FIG. 7, adjustable member 46 may be a screw with a proximal portion that is threadably attached to a cylindrical channel 48 positioned in a distal end of adjustment core 44. A distal portion of adjustable member 46 may be attached to a distal end of movable arm 130, for example by threadable attachment via connector 50. As shown, adjustment mechanism 32 is positioned within sensor guide barrel 136 and moving arm cavity 52 of moving arm 130. A proximal end of cylindrical adjustment core 44 is slidably positioned within a distal end of spring 138, and a knob or projection 54 positioned on a proximal end of cylindrical adjustment core 44 is positioned within and is in abutting engagement with an opening 56 in sensor guide barrel 136 to limit lateral movement of adjustment core 44 within sensor guide barrel 136. Connector 50 is press fit within a cylindrical opening 58 of movable arm 130 and is removably attached to movable arm 130 via pin 60 which is press fit within diametrically opposing openings of connector 50, diametrically opposing openings of movable arm 130, and diametrically opposed openings of adjustable member 46.

Figure 8:
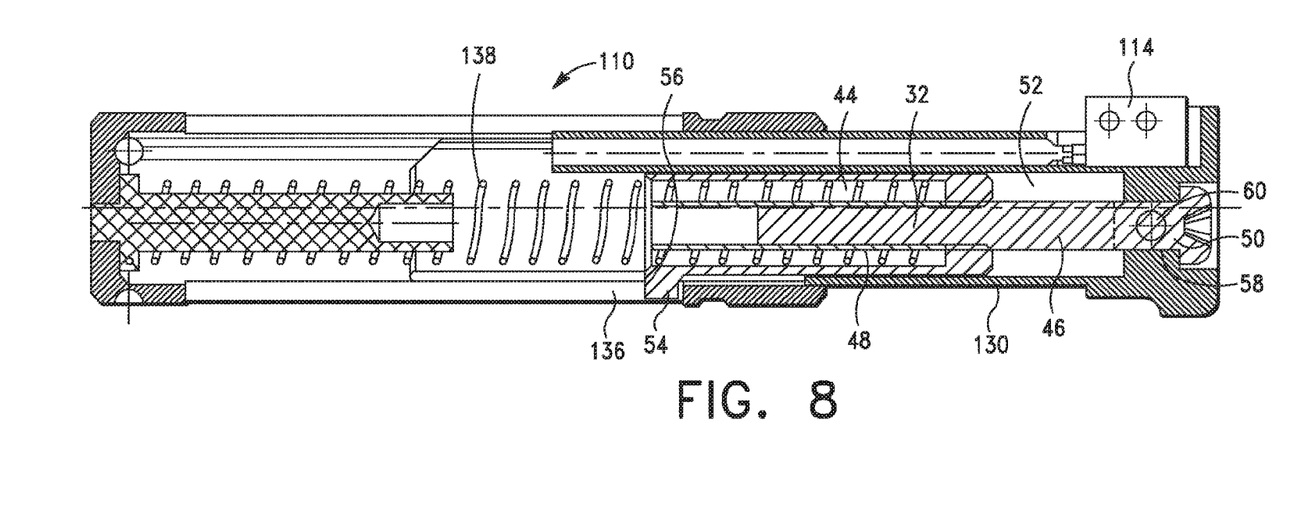
FIG. 8 is a second partial-cross sectional view of the needle sensor assembly shown in FIG. 7.

The spacing between needle sensor 114 and the injection device when needle sensor assembly is in the first extended position is adjusted by simply rotating adjustable member 46. For example, the spacing between needle sensor 114 and the injection device when needle sensor assembly is in the first extended position may be reduced from the position shown in FIG. 7 to the position shown in FIG. 8 by removing connector 50, rotating adjustable member 46 in a clockwise direction until the desired spacing is achieved, and then reattaching connector 50.

FIGS. 1-3 show an exemplary embodiment of on arrangement of the various elements of needle sensor assembly 10. In such an embodiment, needle sensor assembly 10 includes hollow cavity 40, sensor guide barrel 36, movable arm 30, needle sensor 14, sensor needle alignment pin 34, needle sensor return spring 38, and sensor system 22 (shown in FIG. 5). Sensor guide barrel 36 is positioned within hollow cavity 40, which is in turn positioned within sensor assembly mount 62. Needle sensor assembly 10 may also include sensor assembly mount 62. Hollow cavity 40 houses needle sensor return spring 38 and is configured to receive movable arm 30.

Referring to FIGS. 2-3, a portion of sensor wiring 26 is positioned within hollow cavity 40 and is coiled around the sensor guide barrel 36 in order to prevent kinking, as described in more detail with respect to the injection method.

It should be understood that the needle sensor assembly of the present invention may be attached to or used with virtually any injection device that is configured for use with a needle. Suitable injection devices include, but are not limited to, syringes alone or in combination with other components/mechanisms that facilitate injections. It should further be understood that the needle sensor assembly of the present invention may be used in conjunction with injecting animals and/or humans. It should be further understood that needle sensor assembly 10 may be attached to injection device 12 by various mechanisms suitable for the specific injection device, as will be readily understood by one of ordinary skill in the art.

In a second aspect, the present invention is directed to a method of injecting a subject. The method includes the following steps: positioning an injection device against the skin of a subject, wherein a needle is positioned for use in the injection device and the needle sensor assembly is attached to an injection device; pressing a tip of the needle and a distal end of the movable arm against a skin of the subject, wherein the movable arm is in the first extended position; inserting the needle into the skin of the subject at the injection point, wherein as the needle is inserted, the movable arm is pushed to the second retracted position; withdrawing the needle from a subject, wherein the movable arm returns to the first extended position as the needle is withdrawn; wherein the needle sensor detects the presence or absence of a portion of the tip of the needle when the movable arm is returned to the first extended position; and wherein the needle sensor assembly generates a warning if the portion of the tip of the needle is not detected. Needle sensor wiring extending outside of the needle sensor assembly may be positioned in a space between a front body and a handle of the injection device.

In certain embodiments, injections may be performed with injector 16 according to the following exemplary injection method. Referring to FIGS. 6a-b, injection device 12 is positioned against tissue 64 of a subject with needle 18 positioned for use in injection device 12 and needle sensor assembly 10 attached to injection device 12. The tip of needle 18 is pressed into tissue 64 and a portion of needle 18 is momentarily inserted into tissue 64 at an injection point. The distal end of movable arm 30 is simultaneously pressed against the subject's skin, but does not enter into tissue 64. As shown in FIG. 6b-c, pressing injector 16 against the patient causes movable arm 30 to be forced into sensor guide barrel 36, while forcibly biasing needle sensor return spring 38. When needle sensor return spring 38 is forcibly biased as shown in FIGS. 6b-c, needle sensor assembly 10 is in a retracted position. Once the injection is complete, needle 18 is withdrawn, and movable arm 30 simultaneously returns to the first extended position. Needle sensor 14 detects the presence or absence of a portion of the tip of needle 18 when movable arm 30 is in the first extended position, and needle sensor assembly 10 generates a warning if the portion of the tip of needle 18 is not detected.

As needle 18 is pushed into tissue 64, needle sensor 14 remains stationary against tissue 64 and remains aligned towards needle 18. When a portion of needle 18 penetrates tissue 64, needle sensor 14 continues to emit optical beam 20 at a lower portion of needle 18. When the injection is complete and needle 18 is withdrawn from tissue 64, needle sensor return spring 38 slides needle sensor 14 proximally to return needle sensor 14 back to its ready-to-inject position, where needle sensor 14 emits optical beam 20 towards the top portion or tip of needle 18. If, following the injection, any part of needle 18 is broken or no longer in its proper position, optical beam 20 will no longer reflect against needle 18. If a broken needle fragment 66 remains in tissue 64, optical beam 20 will not reflect against a sufficient portion of needle 18.

Needle sensor 14 may be configured to alert the user if needle 18 is missing or bent, regardless of the position of needle sensor 14 or moveable arm 26. For example, when needle sensor 14 is not in the first open/extended position, needle sensor 14 may remain on and pointing toward a lower portion of needle 18. Accordingly, if a lower portion (not limited to a portion of the tip) of needle 18 is not present, needle sensor 14 will detect that needle 18 is not present due to the fact that no optical beam 20 reflects off of needle 18.

When needle 18 is present in front of needle sensor 14, optical beam 20 reflects off of needle 18 and the light is returned to needle sensor 14 and detection is achieved. When needle 18 is not present (or is not sufficiently present or no longer straight and aligned) in front of needle sensor 14, optical beam 20 is not sufficiently reflected off of needle 18 and sensor amplifier unit 24 does not achieve detection. When detection is not achieved (or is achieved at insufficient levels below the threshold detection levels established by the sensor amplifier unit 24), an output signal is emitted by sensor amplifier unit 24. This output signal from sensor amplifier unit 24 may be connected to an audible, tactile or other alarm system to alert the operator that detection of needle 18 has not been achieved. Should a portion of needle 18 become broken or separated, or should needle 18 become bent or misaligned, this insufficient reflection of optical beam 20 back to needle sensor 14 will initiate an alarm sequence from sensor amplifier unit 24. This alarm alerts the operator that needle 18 may be broken, missing, or bent and allows the operator to inspect needle 18 before proceeding further.

When needle sensor 14 and movable arm 30 are moving, most of sensor wiring 26 maintains its shape and position. However, the portion of sensor wiring 26 that is located inside hollow cavity 40 does not maintain its shape and position and is instead coiled around sensor guide barrel 36. The coiled portion of sensor wiring 26 collapses and stretches with each injection cycle, similar to a compression spring. This allows movable arm 30 to move freely, without kinking or compressing sensor wiring 26, so that sensor wiring 26 does not get damaged.

Referring to FIGS. 2-3 and 5, sensor wiring 26 passes through moving arm cavity 52 and hollow cavity 40 and then passes through needle sensor wiring conduit 42. Needle sensor wiring conduit 42 is positioned between hollow cavity 40 and the exterior of needle sensor assembly 10 and allows sensor wiring 26 to pass into the space between the syringe front body 68 and syringe actuator handle 70 of the injection device 12 (the injection device 12 is described more fully below).

An exemplary injection device 12 is shown and described herein for purposes of illustration only. It should be understood that any injection device known in the art may be used in connection with needle sensor assembly 10, and one of ordinary skill in the art will readily understand how to configure needle sensor assembly 10 to attach to various types of injection devices.

Figure 4:
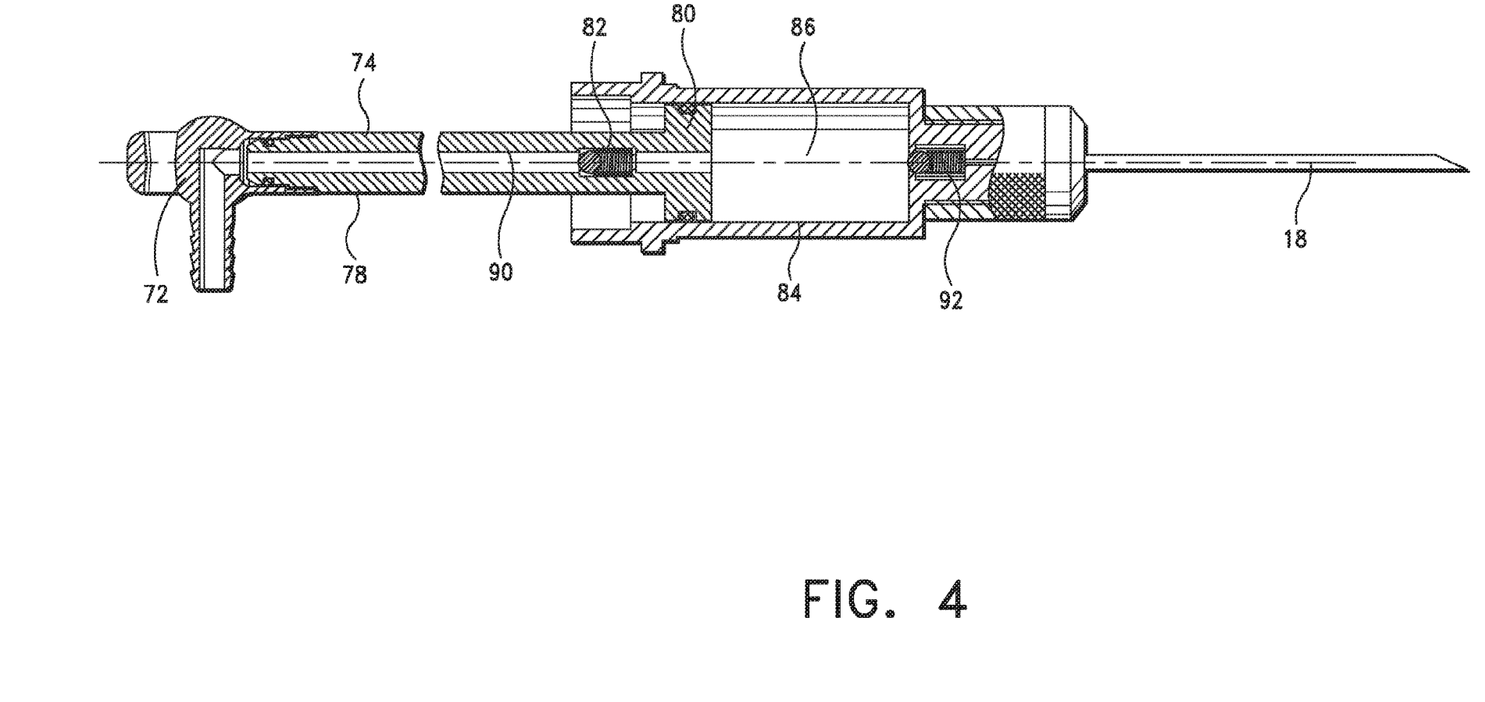
FIG. 4 is a cross-sectional view of the medicine piston assembly of the injection device of the injector of FIG. 1.

Turning to FIGS. 1-2 and 4, in the exemplary injection device 12 depicted in the Figures, a medicine, vaccine, or other injectable product is supplied into injection device 12. A draw off tube (not shown) is attached to medicine adaptor 72, which allows medicine, vaccine, or other injectable product (not shown) to enter medicine plunger piston 74 and fill medicine chamber cavity 84. Injection device 12 is designed to be held and operated with one hand and can be used to administer an injection to a subject. When the operator applies pressure to the proximal side of syringe actuator handle 70, syringe actuator handle 70 pivots relative to actuator axle 76. When syringe actuator handle 70 pivots relative to actuator axle 76, syringe actuator handle 70 pushes medicine piston assembly 78 (shown in FIG. 4) distally. Referring to FIGS. 2 & 4, medicine piston assembly 78 includes a medicine plunger head 80, inlet check valve 82, medicine plunger piston 74 and medicine tube adaptor 72. Medicine plunger head 80 is located on the front end of medicine piston assembly 78. When syringe actuator handle 70 pushes medicine piston assembly 78 distally, medicine plunger head 80 moves distally and this movement reduces the internal volume of medicine chamber cavity 86 which holds the injectable liquid. This reduction of the internal volume of the medicine chamber cavity 86 forces the injectable liquid through the needle 18 and into tissue 64. Check valve 82 prevents the liquid in the medicine chamber cavity 86 from re-entering the medicine plunger piston 74, such that the liquid is expelled only through needle 18 when the internal volume of the medicine chamber cavity 86 is reduced.

The injection is completed when medicine piston assembly 78 stops against medicine chamber 84 and the liquid inside medicine chamber cavity 86 is fully expelled through needle 18. Upon completion of the injection, the operator relaxes their hand or otherwise removes the pressure being applied to syringe actuator handle 70. Without this pressure applied to the proximal side of syringe actuator handle 70 by the operator, torsion spring 88 pushes syringe actuator handle 70 proximally. When syringe actuator handle 70 moves proximally by the force of torsion spring 88, syringe actuator handle 70 pulls medicine piston assembly 78 proximally. This proximal movement of medicine piston assembly 78 enlarges medicine chamber cavity 86. In this phase of the operating cycle, medicine chamber cavity 86 has negative pressure, which allows liquid to flow into medicine chamber cavity 86 via medicine fluid path 90. Medicine chamber cavity 86 is not filled with air through needle 18 because outlet check valve 92 prevents air from flowing into medicine chamber 84 through needle 18.

When torsion spring 88 moves syringe actuator handle 70 proximally to its most proximal position, medicine piston assembly 78 is ready for the next injection cycle. At this point, medicine chamber cavity 86 has reached its preset capacity limit (dose volume setting) and medicine chamber cavity 86 is filled with liquid via medicine fluid path 90. At this point, injection device 12 is once again in the ready-to-inject position.

The dose volume to be injected is determined by the volume of the medicine chamber cavity 86 at the time of injection. The operator can set the injection device 12 at different dose volume settings. In the current embodiment, a dose range of 0.5 ml to 6.0 ml is contemplated, but smaller and larger dose volume ranges are practicable within the scope of this invention. To set the desired dose volume setting of the injection device 12, dose adjusting nut 94 is rotated. The operator rotates dose adjusting nut 94 counterclockwise to increase the dose volume setting and clockwise to decrease the dose volume setting. This rotation of dose adjusting nut 94 changes the stroke of medicine piston assembly 78, which changes the size of, and volume inside, medicine chamber cavity 86. Thus, by rotating dose adjusting nut 94, the operator may change the volume of medicine chamber cavity 86 and the dose volume setting to be injected during operation of injection device 12.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

I claim:

1. A needle sensor assembly comprising:
   a needle sensor housed within the needle sensor assembly, wherein the needle sensor assembly is configured to be attached to an injection device, wherein when the needle sensor assembly is attached to the injection device, the needle sensor is configured to;
   be aligned with and facing a needle positioned for use in the injection device when the needle is positioned for use in the injection device; and
   detect if the needle sensor is no longer aligned with the needle previously positioned for use in the injection device such that the needle is bent, absent from the injection device, or broken; and
   a movable arm on which the needle sensor is carried, wherein the movable arm is movable between a first extended position and a second retracted position, and wherein when the movable arm is in the first extended position, the needle sensor is aligned with a portion of the needle when the needle is positioned for use in the injection device.

2. The needle sensor assembly of claim 1, wherein the movable arm extends generally parallel to a longitudinal axis of the needle when the needle is positioned for use in the injection device.

3. The needle sensor assembly of claim 1, wherein the movable arm is configured to slidably move generally parallel to the longitudinal axis of the needle when the needle is positioned for use in the injection device to maintain alignment of the needle sensor with the longitudinal axis of the needle.

4. The needle sensor assembly of claim 1, wherein the needle sensor is selected from the group consisting of a proximity sensor, an infrared sensor, a passive infrared sensor, an ultrasonic sensor, a magnetic sensor, an inductive sensor or a capacitive sensor.

5. The needle sensor assembly of claim 1, wherein the needle sensor is a fiber optic sensor.

6. The needle sensor assembly of claim 5, wherein the fiber optic sensor is configured to generate an optical beam that extends in a plane that is aligned with the longitudinal axis of the needle when the needle is positioned for use in the injection device.

7. The needle sensor assembly of claim 1, wherein when the movable arm is in the first extended position, the optical beam aligns with at least a portion of the needle when the needle is positioned for use in the injection device.

8. The needle sensor assembly of claim 1, wherein the needle sensor assembly further comprise a spring, wherein the spring is releasably biased against the movable arm when the movable arm is in the first extended position, and wherein the spring is forcibly biased by the movable arm when the movable arm is in the second retracted position.

9. The needle sensor assembly of claim 1, wherein the needle sensor assembly further comprises a hollow cavity which houses the spring, if present, and is configured to receive the movable arm.

10. The needle sensor assembly of claim 9, further comprising needle sensor wiring, wherein at least a portion of the needle sensor wiring is positioned within the hollow cavity.

11. The needle sensor assembly of claim 10, wherein the portion of the needle sensor wiring positioned within the hollow cavity is coiled to prevent kinking.

12. The needle sensor assembly of claim 10, further comprising a sensor guide barrel within the hollow cavity, wherein the spring is housed within the sensor guide barrel and the needle sensor wiring is coiled around the sensor guide barrel.

13. The needle sensor assembly of claim 9, further comprising a needle sensor wiring conduit between the hollow cavity and an exterior of the needle sensor assembly.

14. The needle sensor assembly of claim 1, further comprising a sensor system.

15. The needle sensor assembly of claim 14, wherein the sensor system comprises the needle sensor, the needle sensor wiring, a sensor amplifier unit, and a sensor electrical source.

16. The needle sensor assembly of claim 14, wherein the sensor system is configured to detect when the needle is positioned for use in the injection device.

17. The needle sensor assembly of claim 14, wherein the sensor system is configured to generate a warning when the needle is not detected.

18. A method of injecting a subject, comprising:
positioning an injection device against the skin of a subject, wherein a needle is positioned for use in the injection device and the needle sensor assembly of claim 1 is attached to the injection device;
pressing a tip of the needle against a skin of the subject;
inserting the needle into the skin of the subject at an injection point;
withdrawing the needle from a subject;
wherein the needle sensor detects the presence or absence of a portion of the needle; and
wherein the needle sensor assembly generates a warning if the portion of the needle is not detected.

19. A method of injecting a subject, comprising:
positioning an injection device against the skin of a subject, wherein a needle is positioned for use in the injection device and the needle sensor assembly of claim 1 is attached to the injection device;
pressing a tip of the needle and a distal end of the movable arm against a skin of the subject, wherein the movable arm is in the first extended position;
inserting the needle into the skin of the subject at an injection point, wherein as the needle is inserted, the movable arm is pushed to the second retracted position;
withdrawing the needle from a subject, wherein the movable arm returns to the first extended position as the needle is withdrawn;
wherein the needle sensor detects the presence or absence of a portion of the needle when the movable arm is returned to the first extended positon; and
wherein the needle sensor assembly generates a warning if the portion of the needle is not detected.

20. The method of claim 18, wherein needle sensor wiring extending outside of the needle sensor assembly is positioned in a space between a front body and a handle of the injection device.

21. The needle sensor assembly of claim 1, further comprising an adjustment mechanism configured to adjust a spacing between the needle sensor and the injection device when the movable arm is in the first extended position.

22. The needle sensor assembly of claim 21, wherein the adjustment mechanism comprises
an adjustment core slidably positioned within a sensor guide barrel within a hollow cavity within the needle sensor assembly, wherein a lateral movement of the adjustment core within the sensor guide barrel is limited, and
an adjustment member having a proximal end adjustably attached to the adjustment core and a distal end connected to a distal end of the movable arm.

23. The needle sensor assembly of claim 22, wherein the adjustment member is a screw.

* * * * *